(12) United States Patent
Kawakami

(10) Patent No.: US 12,412,726 B2
(45) Date of Patent: Sep. 9, 2025

(54) X-RAY GENERATION DEVICE AND X-RAY IMAGING SYSTEM

(71) Applicant: HAMAMATSU PHOTONICS K.K., Hamamatsu (JP)

(72) Inventor: Hiroki Kawakami, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 251 days.

(21) Appl. No.: 18/038,262

(22) PCT Filed: Sep. 14, 2021

(86) PCT No.: PCT/JP2021/033744
§ 371 (c)(1),
(2) Date: May 23, 2023

(87) PCT Pub. No.: WO2022/149310
PCT Pub. Date: Jul. 14, 2022

(65) Prior Publication Data
US 2024/0006145 A1    Jan. 4, 2024

(30) Foreign Application Priority Data
Jan. 5, 2021   (JP) .................. 2021-000435

(51) Int. Cl.
*H01J 35/14* (2006.01)
*G01N 23/04* (2018.01)
*G01N 23/083* (2018.01)

(52) U.S. Cl.
CPC ............ *H01J 35/147* (2019.05); *G01N 23/04* (2013.01); *G01N 23/083* (2013.01); *G01N 2223/20* (2013.01)

(58) Field of Classification Search
CPC ............ H01J 35/147; H01J 2235/1262; H01J 35/112; H01J 35/153; H01J 2235/086;
(Continued)

(56) References Cited

U.S. PATENT DOCUMENTS

2014/0307853 A1* 10/2014 Behling ................. H01J 35/10
378/62
2016/0189909 A1   6/2016 Yamanishi et al.

FOREIGN PATENT DOCUMENTS

JP    2002-195961 A    7/2002
JP    2012-520543 A    9/2012
(Continued)

OTHER PUBLICATIONS

International Preliminary Report on Patentability mailed Jul. 20, 2023 for PCT/JP2021/033744.

*Primary Examiner* — Courtney D Thomas
(74) *Attorney, Agent, or Firm* — Faegre Drinker Biddle & Reath LLP

(57) ABSTRACT

An X-ray generation device includes an electron gun emitting an electron beam, an X-ray generation target including a plurality of target parts generating X-rays in response to incidence of the electron beam from the electron gun, and an irradiation area switching unit switching an area of the X-ray generation target irradiated with the electron beam between a first irradiation area and a second irradiation area. The number of target parts included in the first irradiation area is larger than the number of target parts included in the second irradiation area. An area of the target parts included in the first irradiation area is larger than an area of the target parts included in the second irradiation area.

10 Claims, 10 Drawing Sheets

(58) Field of Classification Search
CPC ....... H01J 35/30; G01N 23/04; G01N 23/083; G01N 2223/20; A61B 6/40; G21K 2207/005

See application file for complete search history.

(56) References Cited

FOREIGN PATENT DOCUMENTS

| | | | |
|---|---|---|---|
| JP | 2014-067513 | A | 4/2014 |
| JP | 2015-503190 | A | 1/2015 |
| JP | 2015-028879 | A | 2/2015 |
| JP | 2015-170504 | A | 9/2015 |
| JP | 2016-537797 | A | 12/2016 |
| JP | 6166145 | B2 | 7/2017 |
| WO | WO-2010/103331 | A1 | 9/2010 |
| WO | WO-2013/076598 | A1 | 5/2013 |
| WO | WO-2015/084466 | A2 | 6/2015 |

\* cited by examiner

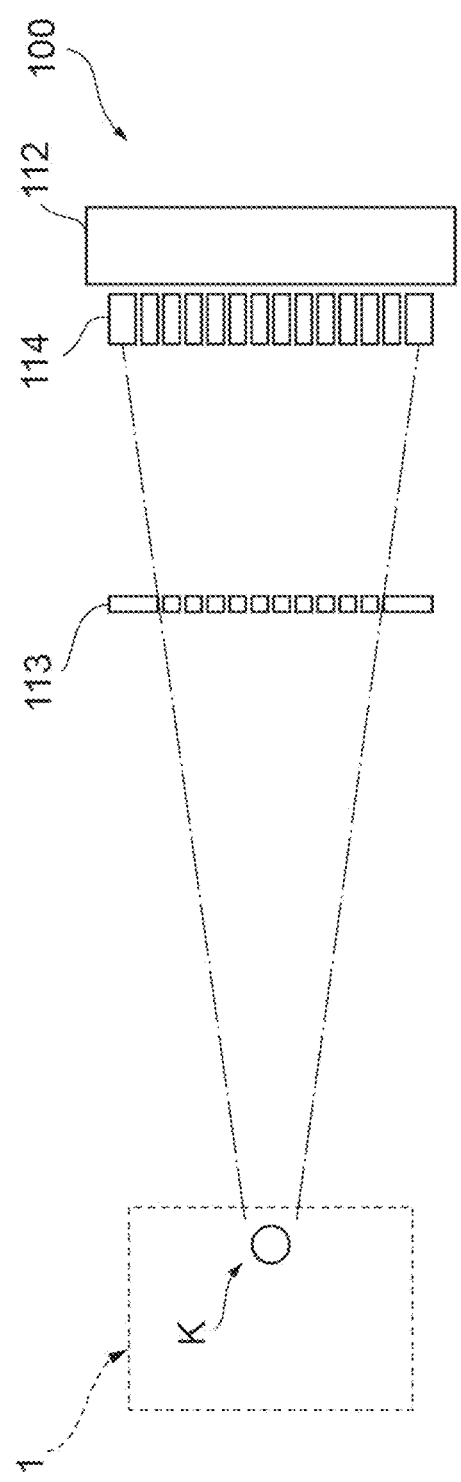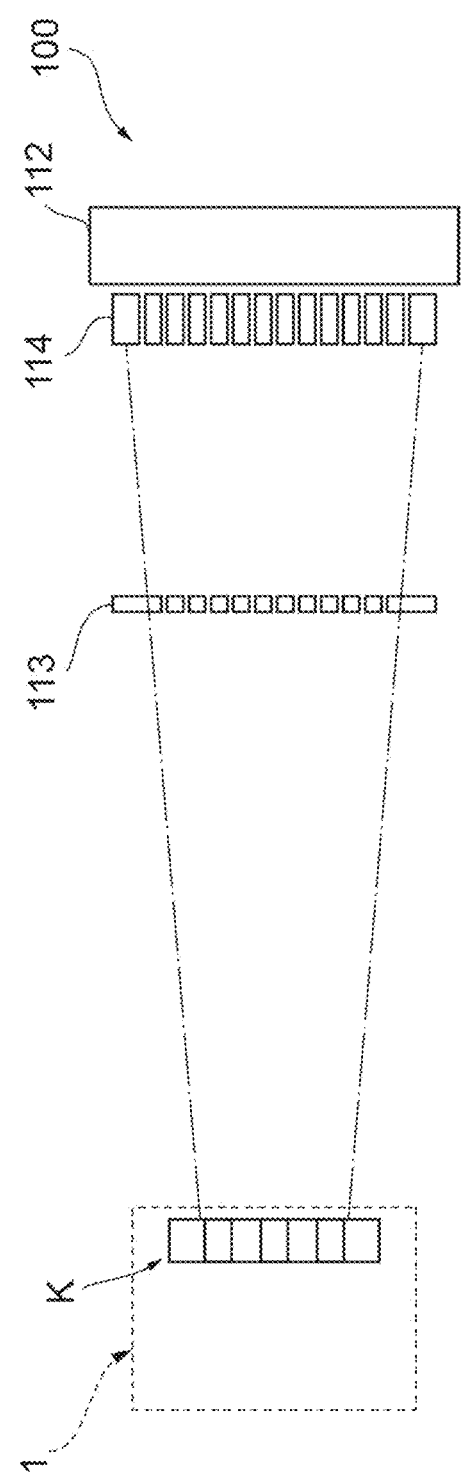
Fig. 4

X-RAY GENERATION DEVICE AND X-RAY IMAGING SYSTEM

TECHNICAL FIELD

The present disclosure relates to an X-ray generation device and an X-ray imaging system.

BACKGROUND ART

An X-ray generator including an electron gun emitting an electron beam and an X-ray generation target including a plurality of target parts generating X-rays in response to incidence of an electron beam is known (for example, see Patent Literature 1). Such an X-ray generator is mounted, for example, in an X-ray imaging system.

CITATION LIST

Patent Literature

[Patent Literature 1] Japanese Unexamined Patent Publication No. 2016-537797

SUMMARY OF INVENTION

Technical Problem

The aforementioned X-ray imaging system can be used, for example, as an X-ray imaging system using an X-ray phase imaging technique. In this case, X-rays emitted from the X-ray generation device are detected by an X-ray detector via an object, a phase grating, and an absorption grating. In such an X-ray imaging system, there may be demand for changing X-ray imaging characteristics (such as a spatial resolution and a required imaging time) according to, for example, the purpose and/or a type of the object. For example, when an object has a fine structure, X-ray imaging with a high spatial resolution is required and thus a Talbot interferometer system can be preferably used. When an object varies with the elapse of time, X-ray imaging for a short time is required and thus a Talbot-Lau interferometer system can be preferably used. On the other hand, when an object is relatively large, it may be preferable that the whole object be imaged using X-ray imaging based on the Talbot-Lau interferometer system for a short time and only a part requiring ascertainment with a high resolution be imaged using X-ray imaging based on the Talbot interferometer system. In this way, when it is desired to change X-ray characteristics, it is necessary to change the X-ray generation device according to required characteristics in the related art. Accordingly, it is difficult to simply change X-ray imaging characteristics.

The present disclosure has been invented to solve the aforementioned problem and provides an X-ray generation device and an X-ray imaging system in which X-ray imaging characteristics can be simply changed.

Solution to Problem

An X-ray generation device according to an aspect of the present disclosure includes: an electron gun emitting an electron beam; an X-ray generation target including a plurality of target parts generating X-rays in response to incidence of the electron beam from the electron gun; and an irradiation area switching unit switching an area of the X-ray generation target irradiated with the electron beam between a first irradiation area and a second irradiation area, wherein the number of target parts included in the first irradiation area is larger than the number of target parts included in the second irradiation area, and an area of the target parts included in the first irradiation area is larger than an area of the target parts included in the second irradiation area when seen in an incidence direction of the electron beam.

In the X-ray generation device, the number of target parts and the magnitude of the area irradiated with the electron beam can be changed by switching the area of the X-ray generation target irradiated with the electron beam using the irradiation area switching unit. As a result, it is possible to switch a mode of X-rays which are generated from the X-ray generation target and to simply switch between two X-ray imaging modes with different characteristics. That is, it is possible to simply change X-ray imaging characteristics.

The irradiation area switching unit may switch the area of the X-ray generation target irradiated with the electron beam between the first irradiation area and the second irradiation area by switching a beam size of the electron beam with which the X-ray generation target is irradiated between a first size and a second size smaller than the first size. In this case, it is possible to realize two X-ray imaging modes with different characteristics by controlling the beam size of an electron beam with which the X-ray generation target is irradiated.

The irradiation area switching unit may switch the area of the X-ray generation target irradiated with the electron beam between the first irradiation area and the second irradiation area by deflecting the electron beam emitted from the electron gun. In this case, it is possible to realize two X-ray imaging modes with different characteristics by controlling deflection of an electron beam emitted from the electron gun.

The electron gun may be able to selectively emit one of a first electron beam and a second electron beam with a beam size larger than the first electron beam, and the irradiation area switching unit may switch the area of the X-ray generation target irradiated with the electron beam between the first irradiation area and the second irradiation area by switching the electron beam emitted from the electron gun between the first electron beam and the second electron beam. In this case, it is possible to realize two X-ray imaging modes with different characteristics by switching the electron beam emitted from the electron gun between the first electron beam and the second electron beam.

The X-ray generation target may include a plurality of linear target parts arranged in parallel to each other as the plurality of target parts, the first irradiation area may span to include at least two linear target parts, and the second irradiation area may span to include only one linear target part. In this case, it is possible to switch an X-ray imaging mode between a mode in which X-rays are generated from the X-ray generation device which is a plurality of light sources and a mode in which X-rays are generated from the X-ray generation device which is a dot light source by switching the area irradiated with the electron beam using the irradiation area switching unit and, for example, to switch the X-ray imaging mode between X-ray imaging corresponding to the Talbot-Lau interferometer system and X-ray imaging corresponding to the Talbot interferometer system.

The X-ray generation target may include a plurality of linear target parts arranged in parallel to each other and a dot target part as the plurality of target parts, the first irradiation area may span to include at least two linear target parts, and the second irradiation area may span to include only one dot target part. In this case, it is possible to switch an X-ray imaging mode between a mode in which X-rays are generated from the X-ray generation device which is a plurality of light sources and a mode in which X-rays are generated from the X-ray generation device which is a dot light source by switching the area irradiated with an electron beam using the irradiation area switching unit and, for example, to switch the X-ray imaging mode between X-ray imaging corresponding to the Talbot-Lau interferometer system and X-ray imaging corresponding to the Talbot interferometer system.

Each of the target parts may be formed continuously as a unified body in the longitudinal direction of the linear target parts or may be formed discretely in the longitudinal direction of the linear target parts. In this case, it is possible to obtain X-rays under different irradiation conditions by configuring the long linear target parts in different forms.

The X-ray generation device may further include: a support member supporting the X-ray generation target; a housing accommodating at least a part of the electron gun, the X-ray generation target, and the support member; and an X-ray exit window which is provided in the housing and through which X-rays generated from the target parts exit to the outside of the housing. In this case, it is possible to provide an X-ray generation device which can be easily handled.

An X-ray imaging system according to another aspect of the present disclosure includes: the X-ray generation device; an X-ray detector detecting X-rays emitted from the X-ray generation device and passing through an object which is an imaging subject; a phase grating provided between the X-ray generation device and the X-ray detector; and an absorption grating provided between the phase grating and the X-ray detector. With the X-ray imaging system, since the X-ray generation device is provided, it is possible to simply change the X-ray imaging characteristics.

Advantageous Effects of Invention

According to the present disclosure, it is possible to provide an X-ray generation device and an X-ray imaging system in which X-ray imaging characteristics can be simply changed.

BRIEF DESCRIPTION OF DRAWINGS

FIG. 4(a) is a diagram schematically illustrating a configuration of an X-ray imaging system in X-ray imaging using a Talbot interferometer system, and FIG. 4(b) is a diagram schematically illustrating a configuration of an X-ray imaging system in X-ray imaging using a Talbot-Lau interferometer system.

DESCRIPTION OF EMBODIMENTS

Hereinafter, an embodiment of an X-ray generator according to an aspect of the present disclosure will be described in detail.

Figure 1:
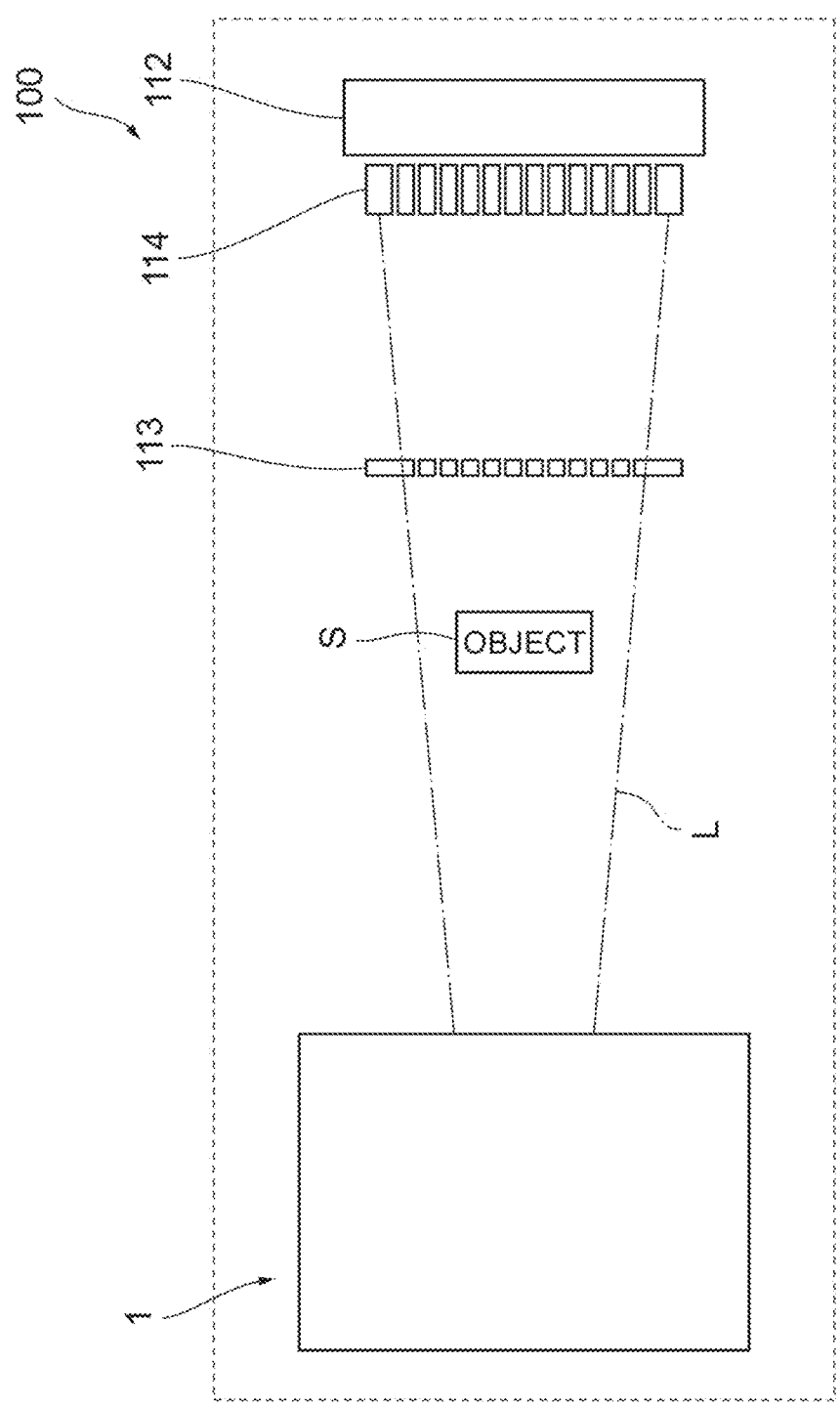
FIG. 1 is a diagram schematically illustrating a configuration of an X-ray imaging system according to an embodiment.

FIG. 1 is a diagram schematically illustrating a configuration of an X-ray imaging system 100 according to an embodiment. As illustrated in FIG. 1, the X-ray imaging system 100 is an X-ray phase imaging system that can generate grayscale (contrast) of an image from differences in intensity and phase of X-rays L passing through an object S which is an imaging subject and acquire an X-ray image, a phase differential image, and a small-angle scattering image of absorption contrast. The X-ray imaging system 100 is, for example, a system that is used for noninvasive inspection of an object S. The X-ray imaging system 100 is a system that can selectively perform X-ray imaging using a Talbot interferometer system and X-ray imaging using a Talbot-Lau interferometer system.

The X-ray imaging system 100 includes, an X-ray generator 1, an X-ray detector 112, a phase grating 113, and an absorption grating 114. The X-ray generator 1 is an X-ray source emitting X-rays L. The X-ray detector 112 detects X-rays L emitted from the X-ray generator 1 and passing through the object S and acquires an image. The phase grating 113 is a grating that is disposed between the X-ray generator 1 and the X-ray detector 112, and is disposed between the object S and the X-ray detector 112 in this embodiment. The phase grating 113 may be disposed in front of the object S or between the X-ray generator 1 and the object S. The phase grating 113 includes a plurality of slits which are arranged at uniform intervals. The phase grating 113 forms a self-image by causing spherical waves diffracted by the slits to interfere with each other (a Talbot effect). The absorption grating 114 is a grating that is disposed between the phase grating 113 and the X-ray detector 112. The absorption grating 114 includes a plurality of slits arranged in a cycle corresponding to the phase grating 113.

In the X-ray imaging system 100, X-rays L emitted from the X-ray generator 1 and passing through the phase grating 113 and the absorption grating 114 form moire fringes, and the moire fringes are detected by the X-ray detector 112. When there is no object S, the moire fringes are linearly arranged at equal intervals. On the other hand, when there is an object S, the fringes of X-rays L passing through the phase grating 113 are deformed by the object S, and the moire fringes are also deformed. The amount of deformation is phase information (corresponding to a phase shift). The moire fringes including deformation can be detected by the X-ray detector 112. Deformation of the fringes of X-rays L passing through the phase grating 113 is small and thus cannot be satisfactorily detected by the X-ray detector 112, but the deformation is enlarged to a size which can be detected as deformation of the moire fringes by providing the absorption grating 114.

Figure 2:
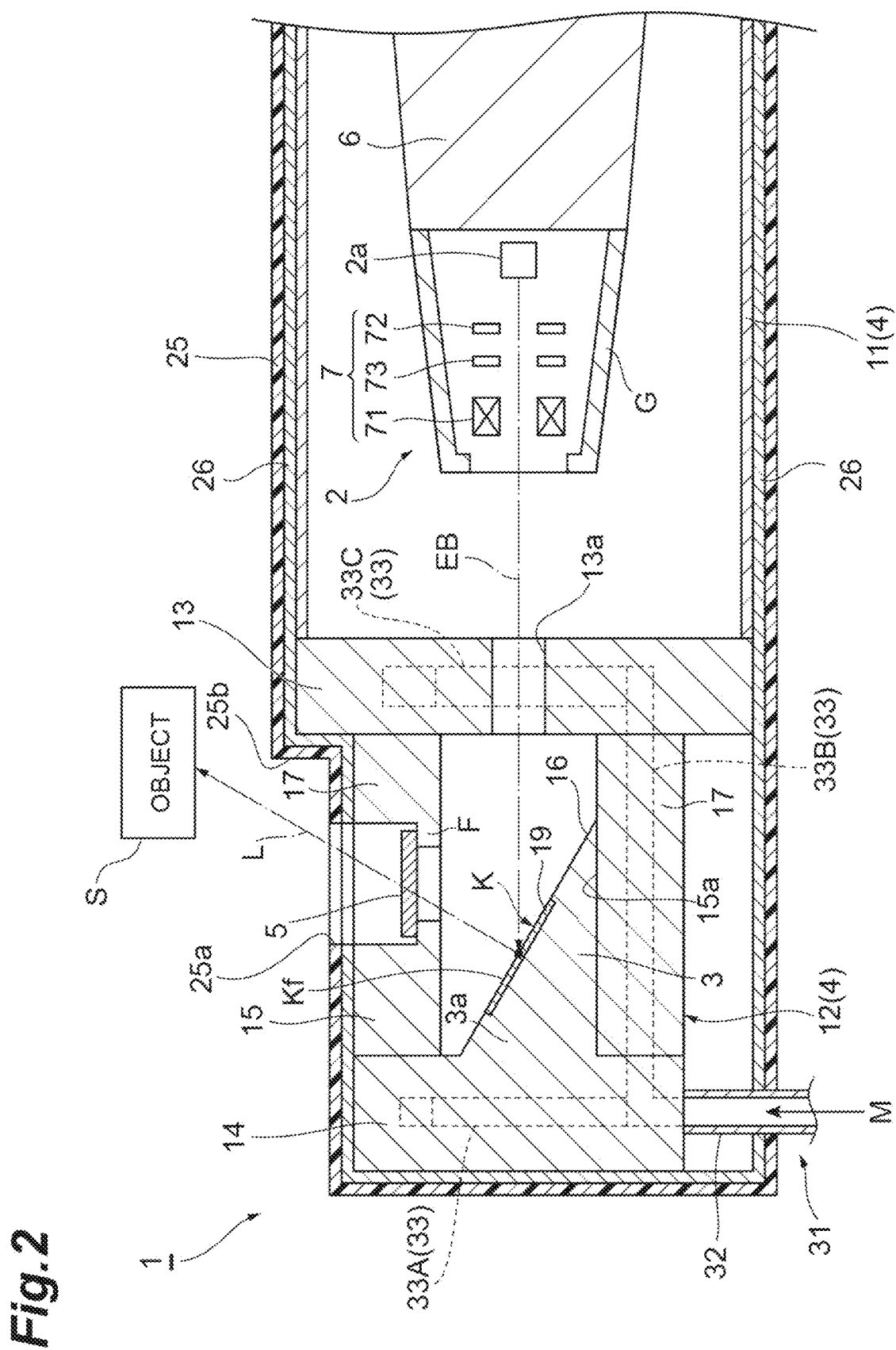
FIG. 2 is a sectional view schematically illustrating an X-ray generator illustrated in FIG. 1.
Figure 3:
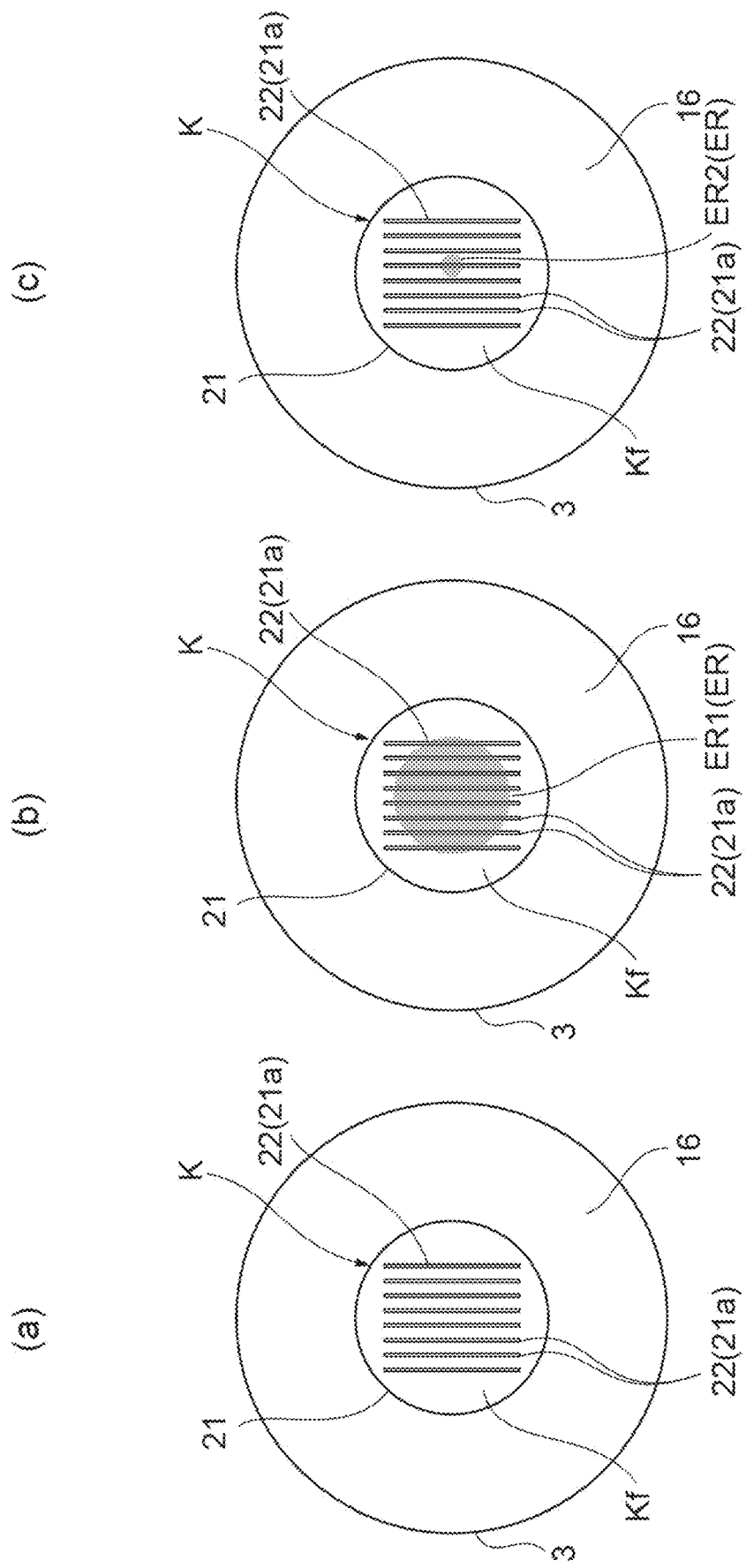
FIG. 3(a) is a plan view illustrating an X-ray generation target illustrated in FIG. 2.
FIG. 3(b) is a plan view illustrating a first irradiation area in the X-ray generation target illustrated in FIG. 3(a)
FIG. 3(c) is a plan view illustrating a second irradiation area in the X-ray generation target illustrated in FIG. 3(a).

FIG. 2 is a sectional view schematically illustrating the X-ray generator 1 illustrated in FIG. 1. FIG. 3 is a perspective view illustrating a support member 3 and a heat dissipation part 14 in FIG. 2. As illustrated in FIG. 2, the X-ray generator 1 includes an electron gun 2, an X-ray generation target K, a support member 3, a housing 4, an X-ray exit window 5, and a cooling mechanism 31. The X-ray generator 1 is a reflection type X-ray tube that takes out X-rays L emitted in a direction crossing an incidence direction of an electron beam EB on the X-ray generation target K.

The electron gun 2 emits an electron beam EB. The electron gun 2 is, for example, a part that generates and emits an electron beam EB having energy of about from several keV to several hundreds of keV. The electron gun 2 includes a filament 2a, a grid G, an irradiation area switching unit 7 which will be described later, and an internal wire electrically connected thereto. The filament 2a constitutes a cathode. The filament 2a is an electron emission member emitting electrons which become an electron beam EB and is formed of, for example, a material including tungsten as a major component. The grid G is an electric field formation member deriving electrons and curbing diffusion of the electrons and is disposed to cover the filament 2a and the irradiation area switching unit 7.

A base part 6 holding the electron gun 2 is formed of, for example, an insulating material such as ceramic or epoxy. A high breakdown voltage type connector (not illustrated) that is supplied with a source voltage of about from several kV to several hundreds of kV from the outside of the X-ray generator 1 is attached to an end of the base part 6. The internal wire connected to the filament 2a or the like is connected to the high breakdown voltage type connector via the inside of the base part 6.

The filament 2a is heated to a high temperature with supply of a current from an external power supply and emits electrons with supply of a negative high voltage of about from—several kV to—several hundreds of kV. Electrons emitted from the filament 2a exit as an electron beam EB from a hole or a slit formed in a part of the grid G. A negative high voltage is applied to the filament 2a, and the housing 4 and the X-ray generation target K (and the support member 3) serving as an anode have a ground potential (an earth potential). Accordingly, the electron beam EB emitted from the electron gun 2 is incident on the X-ray generation target K in a state in which the electron beam is accelerated due to a potential difference between the filament 2a and the X-ray generation target K. In the X-ray generation target K, X-rays L are generated in response to the incident electron beam EB. The size of the electron beam EB (a beam size) at an incidence position on the X-ray generation target K, that is, an irradiation area ER of the electron beam EB (see FIG. 6(a)), is, for example, about φ 1 mm.

The housing 4 accommodates the electron gun 2, the X-ray generation target K, and the support member 3. The housing 4 includes an electron gun accommodation section 11 accommodating the electron gun 2 and a support member accommodation section 12 accommodating the support member 3. The housing 4 constitutes a substantially cylindrical vacuum container as a whole by air-tightly coupling the electron gun accommodation section 11 and the support member accommodation section 12. The electron gun accommodation section 11 is formed in a hollow cylindrical shape out of a metallic material such as stainless steel and is disposed to surround the electron gun 2. A fore-end part (an exit side of an electron beam EB) of the electron gun accommodation section 11 is air-tightly coupled to an aperture part 13 which will be described later of the support member accommodation section 12. For example, an aperture with a circular sectional shape is provided in a base-end part of the electron gun accommodation section 11, and a lid part in which the aforementioned high breakdown voltage type connector is provided is air-tightly coupled to the aperture.

The support member accommodation section 12 is formed of, for example, a metallic material with excellent electrical conductivity and thermal conductivity such as copper. In this embodiment, the support member accommodation section 12 includes an aperture part 13 through which an electron beam EB from the electron gun 2 is introduced to the X-ray generation target K, a heat dissipation part 14 thermally coupled to a base-end part 3a of the support member 3, and a window holding part 15 surrounding the support member 3 and holding the X-ray exit window 5. The window holding part 15 is formed in a hollow cylindrical shape, and the aperture part 13 and the heat dissipation part 14 are formed in a disc shape. The support member accommodation section 12 is formed in a cylindrical shape as a whole to surround the support member 3 by air-tightly coupling the aperture part 13 to one end (the electron gun 2 side) of the window holding part 15 and air-tightly coupling the heat dissipation part 14 to the other end (the opposite side to the electron gun 2) of the window holding part 15.

The aperture part 13 has, for example, a disc shape having substantially the same outer diameter as the outer diameter of the electron gun accommodation section 11. An aperture (13a) with a circular sectional shape penetrating the aperture part in a thickness direction thereof is provided substantially at the center of the aperture part 13. An electron beam EB emitted from the electron gun 2 is introduced into the support member accommodation section 12 via the aperture 13a.

As illustrated in FIG. 2, the heat dissipation part 14 has, for example, a disc shape having a diameter slightly smaller than that of the aperture part 13. In the heat dissipation part 14, the support member 3 protruding toward the aperture part 13 and located in the window holding part 15 is provided on the opposite surface side to the aperture part 13. The support member 3 supports the X-ray generation target K and is formed of, for example, a material with high thermal conductivity such as copper. Here, the support member 3 and the heat dissipation part 14 are formed as a unified body, but they may be separate bodies. One surface of the support member 3 has an arc shape corresponding to an inner circumferential surface 15a of the window holding part 15 and is air-tightly coupled to the inner circumferential surface 15a. Accordingly, the support member 3 protruding toward the aperture part 13 is thermally coupled to the window holding part 15.

The X-ray generation target K is disposed on a target support surface 16 on the other surface side of the support member 3 such that linear target parts 22 which will be described later face the electron gun 2 with a predetermined tilt angle with respect to an emission axis of an electron beam EB. Specifically, a recess 19 is formed in the target support surface 16, and the X-ray generation target K is fitted into the recess 19. The recess 19 is a recess with a shape corresponding to the profile of the X-ray generation target K. An inner surface of the recess 19 comes into contact with the rear surface and the side surface of the X-ray generation target K directly or via a bonding member with high thermal conductivity. The target support surface 16 and a surface Kf of the X-ray generation target K fitted into the recess 19 which is an electron incidence side are flush with each other. That is, the target support surface 16 is disposed on the same plane as the surface Kf of the X-ray generation target K.

The window holding part 15 has a cylindrical shape with the same diameter as that of the heat dissipation part 14. In the window holding part 15, a fixing part F to which the X-ray exit window 5 is fixed is provided in a circumferential wall part 17 facing the target support surface 16. A rectangular aperture smaller than the X-ray exit window 5 is formed in the fixing part F. A circumferential part of the X-ray exit window 5 is bonded to an edge part of the aperture by soldering or the like, and thus the aperture is air-tightly sealed by the X-ray exit window 5. The X-ray exit window 5 fixed to the fixing part F is disposed to face the X-ray generation target K at a predetermined tilt angle.

A case 25 covering the housing 4 is provided in the housing 4. The case 25 is formed in a substantially rectangular parallelepiped shape out of, for example, a conductive material such as metal. In the case an aperture 25a with the same shape as the planar shape of the fixing part F is provided at a position corresponding to the fixing part F of the X-ray exit window 5. An X-ray shielding member 26 is disposed on the inner surface side of the case 25 except for the position of the aperture 25a. The X-ray shielding member 26 is formed of a material with high X-ray shielding capability (for example, a heavy metal material such as lead) and is disposed between the case 25 and the housing 4. Accordingly, unnecessary leakage of X-rays L is curbed, the case 25 and the housing 4 are electrically connected, and the ground potential of the X-ray generator 1 is stably secured.

The cooling mechanism 31 cools the support member accommodation section 12. The cooling mechanism 31 includes a connection pipe 32 for introducing and discharging a coolant and a cooling flow channel 33 for allowing a coolant M to circulate in the wall part of the support member accommodation section 12. The cooling flow channel 33 is a through-hole formed inside of the wall part of the support member accommodation section 12 and is disposed in at least the heat dissipation part 14 and the aperture part 13. The cooling flow channel 33 includes a first cooling flow channel 33A provided in the heat dissipation part 14, a second cooling flow channel 33B provided in the window holding part 15, and a third cooling flow channel 33C provided in the aperture part 13. For example, water or ethylene glycol is used as the coolant M.

The connection pipe 32 is connected to the cooling flow channel 33 and protrudes externally from the case 25. A pair of connection pipes 32 is provided, one connection pipe 32 serves as a pipe for introducing the coolant M into the cooling flow channel 33 from an external circulation device, and the other connection pipe 32 serves as a pipe for discharging the coolant M circulating in the cooling flow channel 33 to the external circulation device. In the cooling mechanism 31, a coolant introduced via the one connection pipe 32 flows in the first cooling flow channel 33A and is discharged from the other connection pipe 32. A part of the coolant introduced into the first cooling flow channel 33A via the one connection pipe 32 branches from the first cooling flow channel 33A, flows in the second cooling flow channel 33B, and is introduced into the third cooling flow channel 33C. The coolant flowing in the third cooling flow channel 33C flows in the second cooling flow channel 33B, returns to the first cooling flow channel 33A, and is discharged from the other connection pipe 32.

In the X-ray generator 1 having the aforementioned configuration, an electron beam EB is incident on the target parts 22 which will be described later on the X-ray generation target K, and X-rays L generated from the X-ray generation target K in response to incidence of the electron beam EB is transmitted by the X-ray exit window 5 and is taken out externally from the X-ray generator 1.

FIG. 3(a) is a plan view illustrating the X-ray generation target K. FIG. 3(b) is a plan view illustrating a first irradiation area ER1. FIG. 3(c) is a plan view illustrating a second irradiation area ER2. In FIGS. 3(a) to 3(c), dimensional ratios in the drawings do not necessarily match those of actual objects to be described (which is true in the subsequent drawings). As illustrated in FIG. 3(a), the X-ray generation target K includes a plurality of long linear target parts (target parts) 22 generating X-rays L in response to incidence of an electron beam EB thereon and a target part holding plate 21 in which the plurality of linear target parts 22 is buried to be parallel with each other.

The target part holding plate 21 is, for example, a panel-shaped member formed of a material with a higher thermal conductivity than the material of the linear target parts 22 such as single-crystal diamond, polycrystalline diamond, or copper. The thermal conductivity of the material of the target part holding plate 21 may be equal to or higher than the thermal conductivity of the material of the support member 3. The target part holding plate 21 has a disk shape. A plurality of bottomed grooves 21a with a rectangular sectional shape are formed in a surface 21f of the target part holding plate 21 which is a surface on which an electron beam is incident over the entire surface thereof. The plurality of grooves 21a extends linearly in parallel to each other. The linear target parts 22 are formed of, for example, metal such as tungsten. The linear target parts 22 are provided in the target part holding plate 21 to fill the grooves 21a and extend linearly in parallel to each other. That is, each linear target part 22 is continuously as a unified body in the longitudinal direction.

For example, the diameter of the target part holding plate 21 ranges from 3 mmϕ to 12 mmϕ, and the thickness of the target part holding plate 21 ranges from 0.1 mm to 3 mm. The pitch of the target parts 22 (an inter-center distance between neighboring linear target parts 22) ranges from 5 µm to 20 µm, the width of the linear target parts 22 ranges from 2 µm to 10 µm, and the depth of the linear target parts 22 ranges from 5 µm to 30 µm.

As illustrated in FIGS. 2, 3(a), and 3(b), the X-ray generation device 1 includes an irradiation area switching unit 7 switching the irradiation area ER of the X-ray generation target K irradiated with an electron beam EB between a first irradiation area ER1 and a second irradiation area ER2. The irradiation area switching unit 7 is provided in the electron gun 2. The irradiation area switching unit 7 includes a deflecting coil 71, a first electrode 72, and a second electrode 73. The deflecting coil 71 adjusts a position of an electron beam EB in a direction perpendicular to an emission axis of the electron beam EB. The first electrode 72 adjusts an amount of electrons of the electron beam EB emitted from the filament 2a. The first electrode 72 is disposed between the filament 2a and the deflecting coil 71. The second electrode 73 adjusts a beam size of an electron beam EB by changing a voltage thereof. The second electrode 73 is disposed between the first electrode 72 and the deflecting coil 71.

In this embodiment, the irradiation area switching unit 7 switches the irradiation area ER between the first irradiation area ER1 and the second irradiation area ER2 by switching a beam size of an electron beam EB with which the X-ray generation target K is irradiated between a first size and a second size smaller than the first size. Here, a beam size is a size of an irradiation area of an electron beam EB with which the X-ray generation target K is irradiated, is substantially the same as the size of the irradiation area ER, and may be referred to as a beam diameter of an electron beam EB with which the X-ray generation target K is irradiated in this embodiment. The beam size may be a magnitude of an area of the irradiation area of an electron beam EB with which the X-ray generation target K is irradiated. The beam diameter of an electron beam EB is a diameter when a beam shape is circular, a diameter in a longitudinal direction when the beam shape is elliptical, or a diameter of an inscribed circle when the beam shape is a polygonal shape or a shape similar thereto, and these diameters are used to compare the beam diameters. The first irradiation area ER1 is an area spanning to include at least two linear target parts 22 in a view in the incidence direction of an electron beam EB (hereinafter also simply referred to as an "incidence direction"). The second irradiation area ER2 is an area spanning to include only one linear target part 22 in the view in the incidence direction. The number of linear target parts 22 included in the first irradiation area ER1 is larger than the number of linear target parts 22 included in the second irradiation area ER2. In a view in the incidence direction, the area of the linear target parts 22 included in the first irradiation area ER1 is larger than the area of the linear target parts 22 included in the second irradiation area ER2.

An example of an optical system alignment method in the X-ray imaging system 100 will be described below.

First, the irradiation area switching unit 7 switches the irradiation area ER to the second irradiation area ER2 (see FIG. 3(c)). Accordingly, as illustrated in FIG. 4(a), X-rays are emitted from the X-ray generation device 1 which is a dot light source, and X-ray imaging using the Talbot interferometer system is performed. In the X-ray imaging using the Talbot interferometer system, an image is sharp and an imaging time is long. At this time, an object S is not provided.

A positional relationship between the phase grating 113 and the absorption grating 114 is determined based on a result of X-ray imaging using the Talbot interferometer system. Specifically, the phase grating 113 and the absorption grating 114 are disposed at predetermined positions (positions which are separated by a set distance from the X-ray generation device 1). The absorption grating 114 is rotated around an optical axis of X-rays L in a state in which the phase grating 113 is fixed, and the position in the rotating direction of the absorption grating 114 is set to a position at which moire fringes are formed in an image detected by the X-ray detector 112. The absorption grating 114 is rotated around the optical axis of X-rays L in a state in which the phase grating 113 is fixed. When the moire fringes rotate as a result, the absorption grating 114 is moved to one side and/or the other side in the optical axis direction of X-rays in a state in which the phase grating 113 is fixed. Then, the absorption grating 114 is rotated around the optical axis of X-rays L again in a state in which the phase grating 113 is fixed. When the moire fringes are not rotated in spite of rotation of the absorption grating 114 in a state in which the phase grating 113 is fixed, the absorption grating 114 is rotated in a state in which the phase grating 113 is fixed and the position in the rotating direction of the absorption grating 114 is set to a position at which the interval of the moire fringes are maximized.

Subsequently, the irradiation area switching unit 7 switches the irradiation area ER to the first irradiation area ER1 (see FIG. 3(b)). Accordingly, as illustrated in FIG. 4(b), X-rays L are emitted from the X-ray generation device 1 which is a plurality of light sources, and X-ray imaging using the Talbot-Lau interferometer system is performed. In the X-ray imaging using the Talbot-Lau interferometer system, an image is less clear and an imaging time is shorter in comparison with X-ray imaging using the Talbot interferometer system. At this time, an object S is not provided. Physical replacement and positioning in the X-ray generation device 1 are not necessary.

The phase grating 113 and the absorption grating 114 are rotated together by the same angle in the same direction around the optical axis of X-rays L, and the positions in the rotating direction thereof are set to positions at which moire fringes are formed in an image detected by the X-ray detector 112. The phase grating 113 and the absorption grating 114 are rotated together by the same angle in the same direction around the optical axis of X-rays L, and the positions in the rotating direction thereof are set to positions at which visibility is maximized. In this way, optical system alignment is completed.

Visibility indicates a degree of grayscale (contrast) of the moire fringes. When the visibility is maximized, the contrast of the moire fringes are maximized, and sensitivity to a phase shift (a phase shift due to an object S) is maximized. In this case, for example, even a thin object S can be imaged.

In the X-ray generation device 1 and the X-ray imaging system 100, the number of target parts 22 and the magnitude of the area irradiated with the electron beam EB can be changed by switching the irradiation area ER of the X-ray generation target K using the irradiation area switching unit 7. As a result, it is possible to switch a mode of X-rays which are generated from the X-ray generation target K and to simply switch two X-ray imaging modes with different characteristics. That is, it is possible to simply change X-ray imaging characteristics.

In the X-ray generation device 1 and the X-ray imaging system 100, the irradiation area switching unit 7 switches the irradiation area ER of the X-ray generation target K between the first irradiation area ER1 and the second irradiation area ER2 by switching the beam size of the electron beam EB with which the X-ray generation target K is irradiated between the first size and the second size smaller than the first size. In this case, it is possible to realize two X-ray imaging modes with different characteristics by controlling the beam size of an electron beam EB with which the X-ray generation target is irradiated.

In the X-ray generation device 1 and the X-ray imaging system 100, the X-ray generation target K includes a plurality of linear target parts 22 arranged in parallel to each other. The first irradiation area ER1 spans to include at least two linear target parts 22, and the second irradiation area ER2 spans to include only one linear target part 22. In this case, it is possible to switch an X-ray imaging mode between a mode in which X-rays L are generated from the X-ray generation device 1 which is a plurality of light sources and a mode in which X-rays L are generated from the X-ray generation device 1 which is a dot light source by switching the irradiation area ER using the irradiation area switching unit 7. It is possible to simply switch the X-ray imaging mode between X-ray imaging corresponding to the Talbot-Lau interferometer system and X-ray imaging corresponding to the Talbot interferometer system.

The X-ray generation device 1 and the X-ray imaging system 100 further includes the support member 3 supporting the X-ray generation target K, the housing 4 accommodating the electron gun 2, the X-ray generation target K, and the support member 3, and the X-ray exit window 5 provided in the housing 4. In this case, it is possible to provide a reflection type X-ray generation device.

The present disclosure is not limited to the embodiment.

In the embodiment, the irradiation area switching unit 7 switches the irradiation area ER between the first irradiation area ER1 and the second irradiation area ER2 by switching the beam size of an electron beam EB, but the present disclosure is not limited thereto. The irradiation area switching unit 7 may switch the irradiation area ER in the X-ray generation target K between the first irradiation area ER1 and the second irradiation area ER2 by deflecting an electron beam EB emitted from the electron gun 2. In this case, it is possible to realize two X-ray imaging modes with different characteristics by controlling deflection of the electron beam EB emitted from the electron gun 2.

In the embodiment, the electron gun 2 may be able to selectively emit one of a first electron beam and the second electron beam with a larger beam size than the first electron beam. For example, the electron gun 2 may include a first filament emitting the first electron gun and a second filament emitting the second electron gun as a cathode. At this time, an electron beam emitting part switching unit is provided as the irradiation area switching unit, and the electron beam emitting part switching unit switches the electron beam EB emitted from the electron gun 2 between the first electron beam and the second electron beam by switching an electron emission source to be used between the first filament and the second filament. That is, the electron beam emitting part switching unit switches an electron beam EB to be emitted from the electron gun 2 between a case in which the electron beam is emitted from the first filament and a case in which the electron beam is emitted from the second filament. Then, the irradiation area ER in the X-ray generation target K may be switched between the first irradiation area ER1 and the second irradiation area ER2 by causing the irradiation area switching unit 7 to perform adjustment such that the X-ray generation target K is appropriately irradiated with the electron beams EB. In this case, it is possible to realize two X-ray imaging modes with different characteristics by switching an electron beam EB to be emitted from the electron gun 2 between the first electron beam and the second electron beam. When the X-ray generation target K is appropriately irradiated with the electron beams EB by only causing the electron beam emitting part switching unit to switch the emission source between the first filament and the second filament, adjustment in the irradiation area switching unit 7 may not be performed. The first filament and the second filament may be together set to a state in which electrons can be emitted therefrom, and the irradiation area switching unit 7 may switch between a case in which an electron beam is emitted from the first filament and a case in which an electron beam is emitted from the second filament. In this case, the electron beam emitting part switching unit is not necessary.

In the embodiment, the X-ray generation target K, the first irradiation area ER1, and the second irradiation area ER2 are not particularly limited. As described in the following modified examples, the number of target parts included in the first irradiation area ER1 has only to be larger than that of the second irradiation area ER2, and the area of the target parts included in the first irradiation area ER1 has only to be larger than that of the second irradiation area ER2 in a view in the incidence direction.

Figure 5:
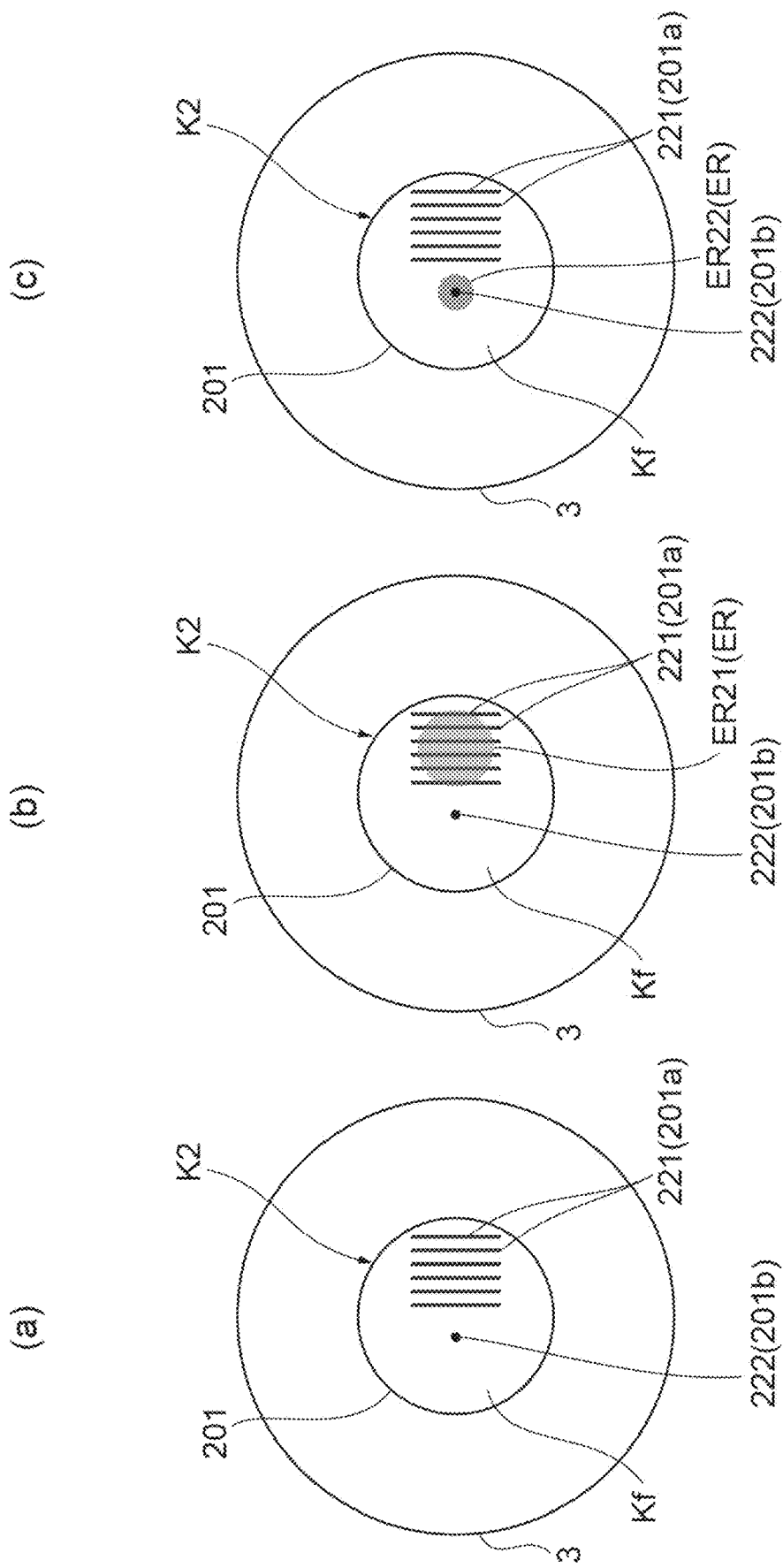
FIG. 5(a) is a plan view illustrating an X-ray generation target according to a modified example.
FIG. 5(b) is a plan view illustrating a first irradiation area in the X-ray generation target illustrated in FIG.
FIG. 5(c) is a plan view illustrating a second irradiation area in the X-ray generation target illustrated in FIG. 5(a).

For example, as illustrated in FIGS. 5(*a*), 5(*b*), and 5(*c*), an X-ray generation target K2 according to a modified example includes a plurality of long linear target parts (target parts) 221 arranged in parallel to each other, one dot target part (target part) 222, and a target part holding plate 201 in which the linear target parts 221 and the dot target part 222 are embedded. In the target part holding plate 201, a plurality of grooves 201*a* extending linearly in parallel to each other and a recess 201*b* separated from the plurality of grooves 201*a* are formed. The linear target parts 221 are provided in the target part holding plate 201 to fill the grooves 201*a*, and extend linearly in parallel to each other. The dot target part 222 is provided in the target part holding plate 201 to fill the recess 201*b* and is separated from the plurality of linear target parts 221. A first irradiation area ER21 according to the modified example spans to include at least two linear target parts 221. A second irradiation area ER22 according to the modified example spans to include only one dot target part 222. The irradiation area switching unit 7 switches the irradiation area ER between the first irradiation area ER21 and the second irradiation area ER22 by switching the beam size of an electron beam EB between the first size and the second size and deflecting the electron beam EB emitted from the electron gun 2 or switching the electron beam EB emitted from the electron gun 2 between the first electron beam and the second electron beam.

Accordingly, it is possible to switch an X-ray imaging mode between a mode in which X-rays L are generated from the X-ray generation device 1 which is a plurality of light sources and a mode in which X-rays L are generated from the X-ray generation device 1 which is a dot light source by switching the irradiation area ER using the irradiation area switching unit 7. It is possible to simply switch the X-ray imaging mode between X-ray imaging corresponding to the Talbot-Lau interferometer system and X-ray imaging corresponding to the Talbot interferometer system.

Figure 6:
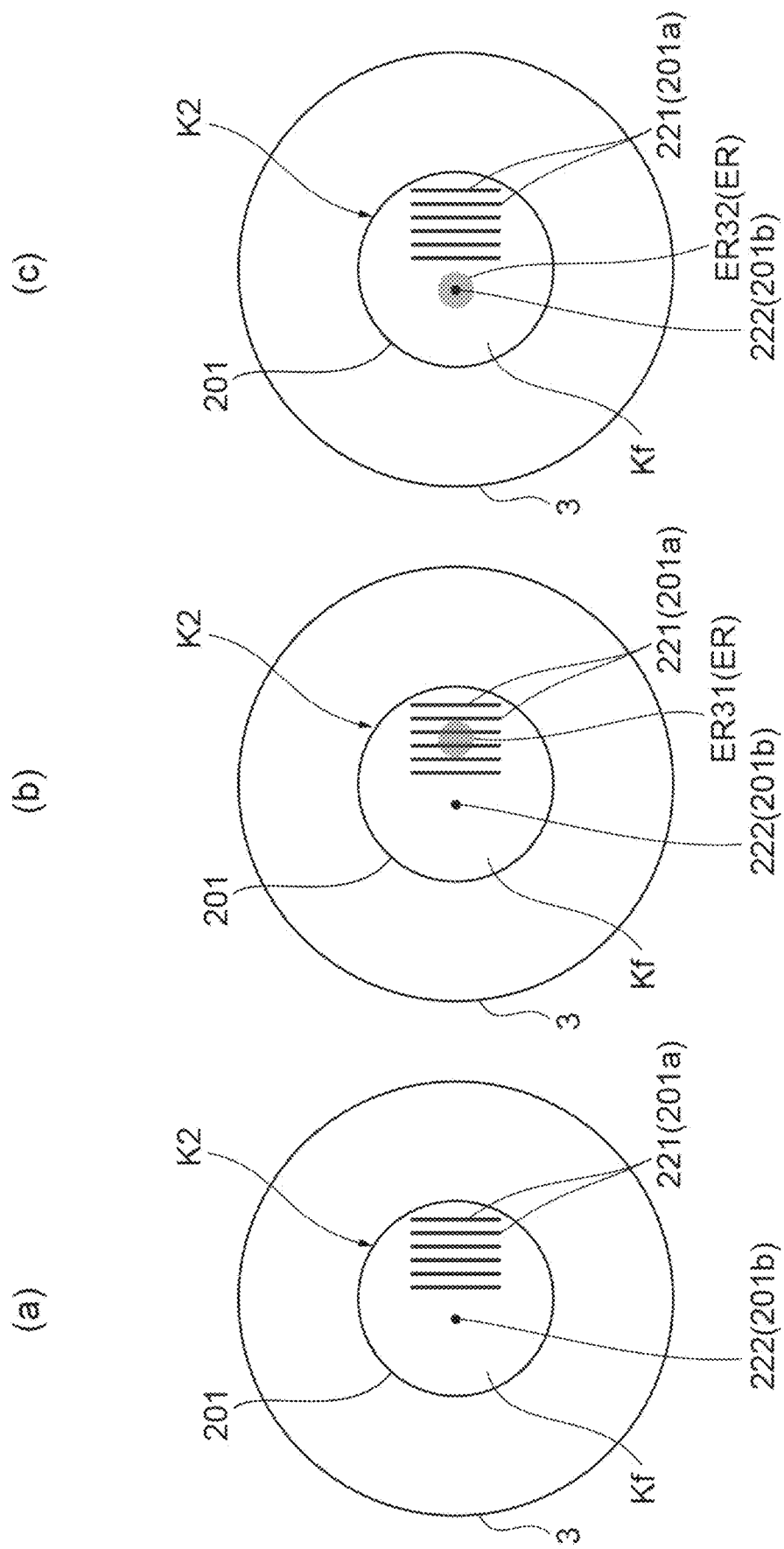
FIG. 6(a) is a plan view illustrating an X-ray generation target according to a modified example.
FIG. 6(b) is a plan view illustrating a first irradiation area in the X-ray generation target illustrated in FIG. 6(a)
FIG. 6(c) is a plan view illustrating a second irradiation area in the X-ray generation target illustrated in FIG. 6(a).

For example, as illustrated in FIGS. 6(*a*), 6(*b*), and 6(*c*), a first irradiation area ER31 according to a modified example spans to include at least two linear target parts 221. A second irradiation area ER32 according to the modified example spans to include only one dot target part 222. The irradiation area switching unit 7 switches the irradiation area ER between the first irradiation area ER31 and the second irradiation area ER32 by deflecting the electron beam EB emitted from the electron gun 2 or switching the electron beam EB emitted from the electron gun 2 between the first electron beam and the second electron beam without switching the beam size of an electron beam EB. Accordingly, similarly to the aforementioned modified example, it is possible to simply switch the X-ray imaging mode between X-ray imaging corresponding to the Talbot-Lau interferometer system and X-ray imaging corresponding to the Talbot interferometer system.

Figure 7:
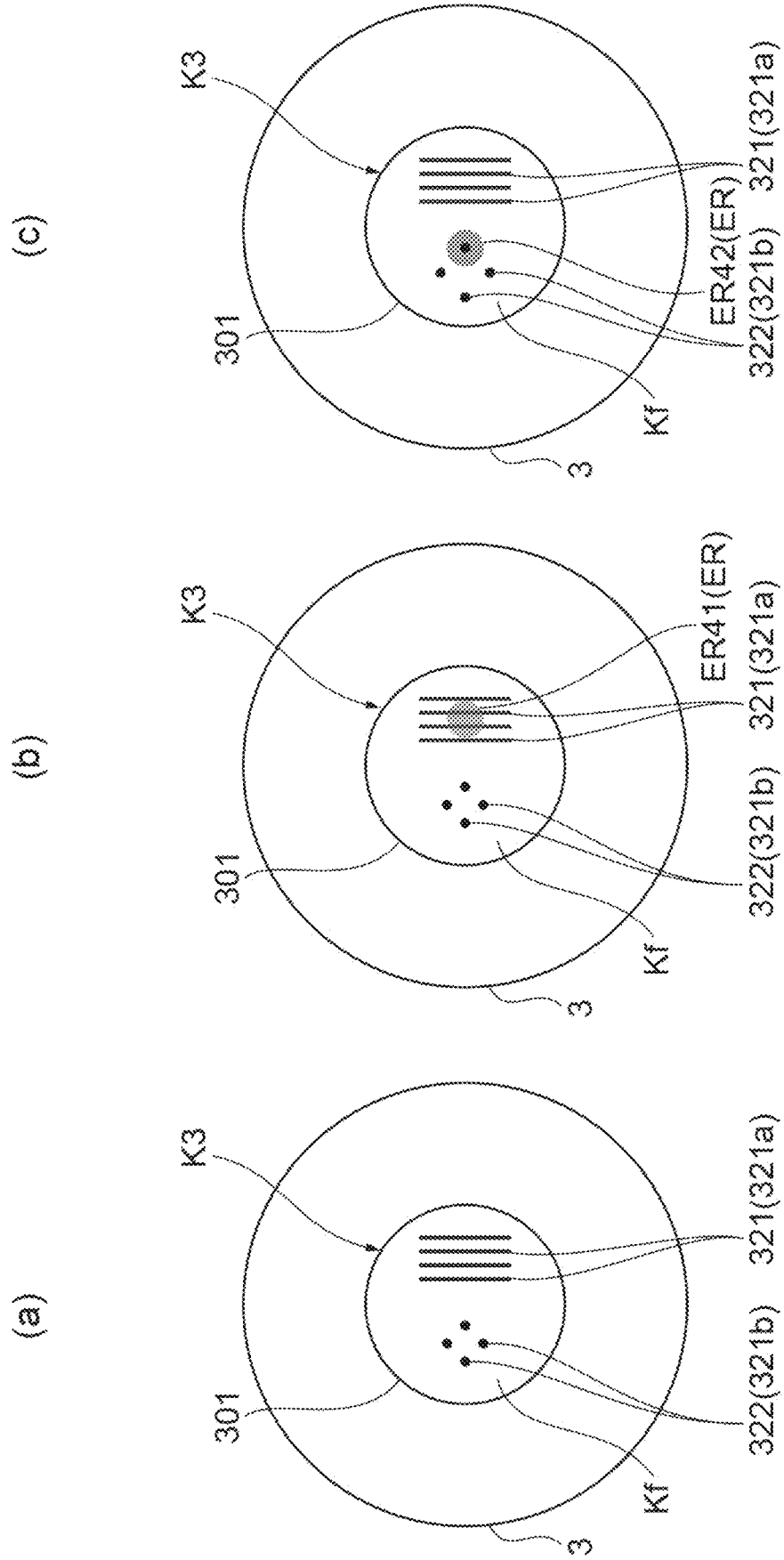
FIG. 7(a) is a plan view illustrating an X-ray generation target according to a modified example.
FIG. 7(b) is a plan view illustrating a first irradiation area in the X-ray generation target illustrated in FIG. 7(a)
FIG. 7(c) is a plan view illustrating a second irradiation area in the X-ray generation target illustrated in FIG. 7(a).

For example, as illustrated in FIGS. 7(*a*), 7(*b*), and 7(*c*), an X-ray generation target K3 according to a modified example includes a plurality of long linear target parts (target parts) 321 arranged in parallel to each other, a plurality of (four herein) dot target parts (target part) 322, and a target part holding plate 301 in which the linear target parts 321 and the dot target parts 322 are embedded. In the target part holding plate 301, a plurality of grooves 301*a* extending linearly in parallel to each other and a plurality of recesses 301*b* separated from the plurality of grooves 201*a* are formed. The linear target parts 321 are provided in the target part holding plate 301 to fill the grooves 301*a*, and extend linearly in parallel to each other. The dot target parts 322 are provided in the target part holding plate 301 to fill the recesses 301*b* and are separated from the plurality of linear target parts 321. A first irradiation area ER41 according to the modified example spans to include at least two linear target parts 321. A second irradiation area ER42 according to the modified example spans to include only one of the plurality of dot target parts 322. The irradiation area switching unit 7 switches the irradiation area ER between the first irradiation area ER41 and the second irradiation area ER42 by deflecting the electron beam EB emitted from the electron gun 2 or switching the electron beam EB emitted from the electron gun 2 between the first electron beam and the second electron beam without switching the beam size of the electron beam EB. Accordingly, similarly to the aforementioned modified examples, it is possible to simply switch the X-ray imaging mode between X-ray imaging corresponding to the Talbot-Lau interferometer system and X-ray imaging corresponding to the Talbot interferometer system. Since the plurality of dot target parts 322 is provided, the dot target parts 322 can be reliably included in the second irradiation area ER42.

Figure 8:
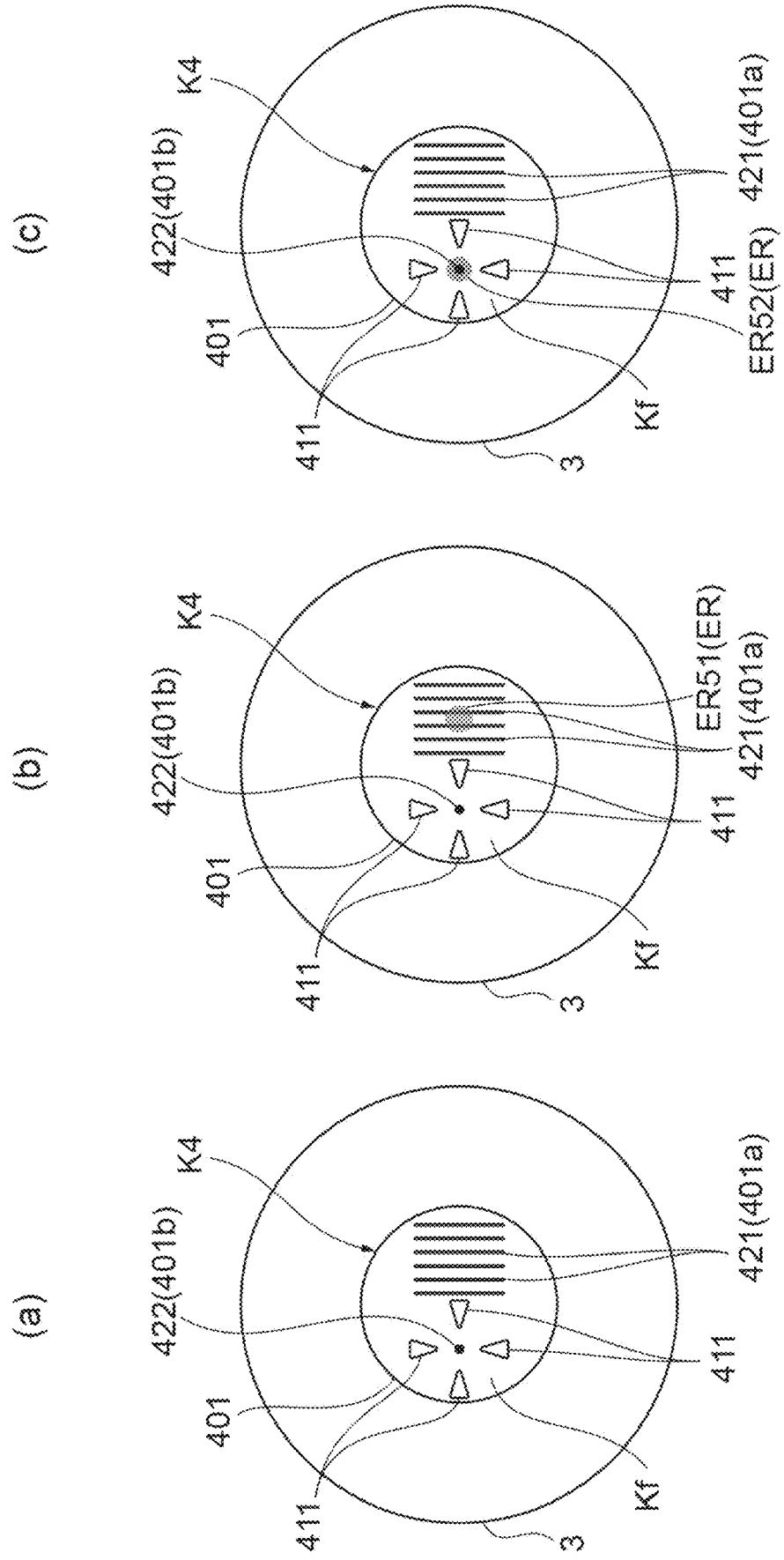
FIG. 8(a) is a plan view illustrating an X-ray generation target according to a modified example.
FIG. 8(b) is a plan view illustrating a first irradiation area in the X-ray generation target illustrated in FIG. 8(a)
FIG. 8(c) is a plan view illustrating a second irradiation area in the X-ray generation target illustrated in FIG. 8(a).

For example, as illustrated in FIGS. 8(*a*), 8(*b*), and 8(*c*), an X-ray generation target K4 according to a modified example includes a plurality of long linear target parts (target parts) 421 arranged in parallel to each other, one dot target part (target part) 422, a target part holding plate 301 in which the linear target parts 421 and the dot target part 422 are embedded, and a mark part 411 provided at a plurality of (four herein) positions around the dot target part 422. In the target part holding plate 401, a plurality of grooves 401*a* extending linearly in parallel to each other and a recess 401*b* separated from the plurality of grooves 401*a* are formed. The linear target parts 421 are provided in the target part holding plate 401 to fill the grooves 401*a*, and extend linearly in parallel to each other. The dot target part 422 is provided in the target part holding plate 301 to fill the recess 401*b* and is separated from the plurality of linear target parts 421. The mark parts 411 are for easily ascertaining the position of the dot target part 422 and may be, for example, one of a printed part, a recessed part, and a protruded part.

A first irradiation area ER51 according to the modified example spans to include at least two linear target parts 421. A second irradiation area ER52 according to the modified example spans to include only one dot target part 422. The irradiation area switching unit 7 switches the irradiation area ER between the first irradiation area ER51 and the second irradiation area ER52 by deflecting the electron beam EB emitted from the electron gun 2 or switching the electron beam EB emitted from the electron gun 2 between the first electron beam and the second electron beam without switching the beam size of the electron beam EB. Accordingly, similarly to the aforementioned modified examples, it is possible to simply switch the X-ray imaging mode between X-ray imaging corresponding to the Talbot-Lau interferometer system and X-ray imaging corresponding to the Talbot interferometer system.

Figure 9:
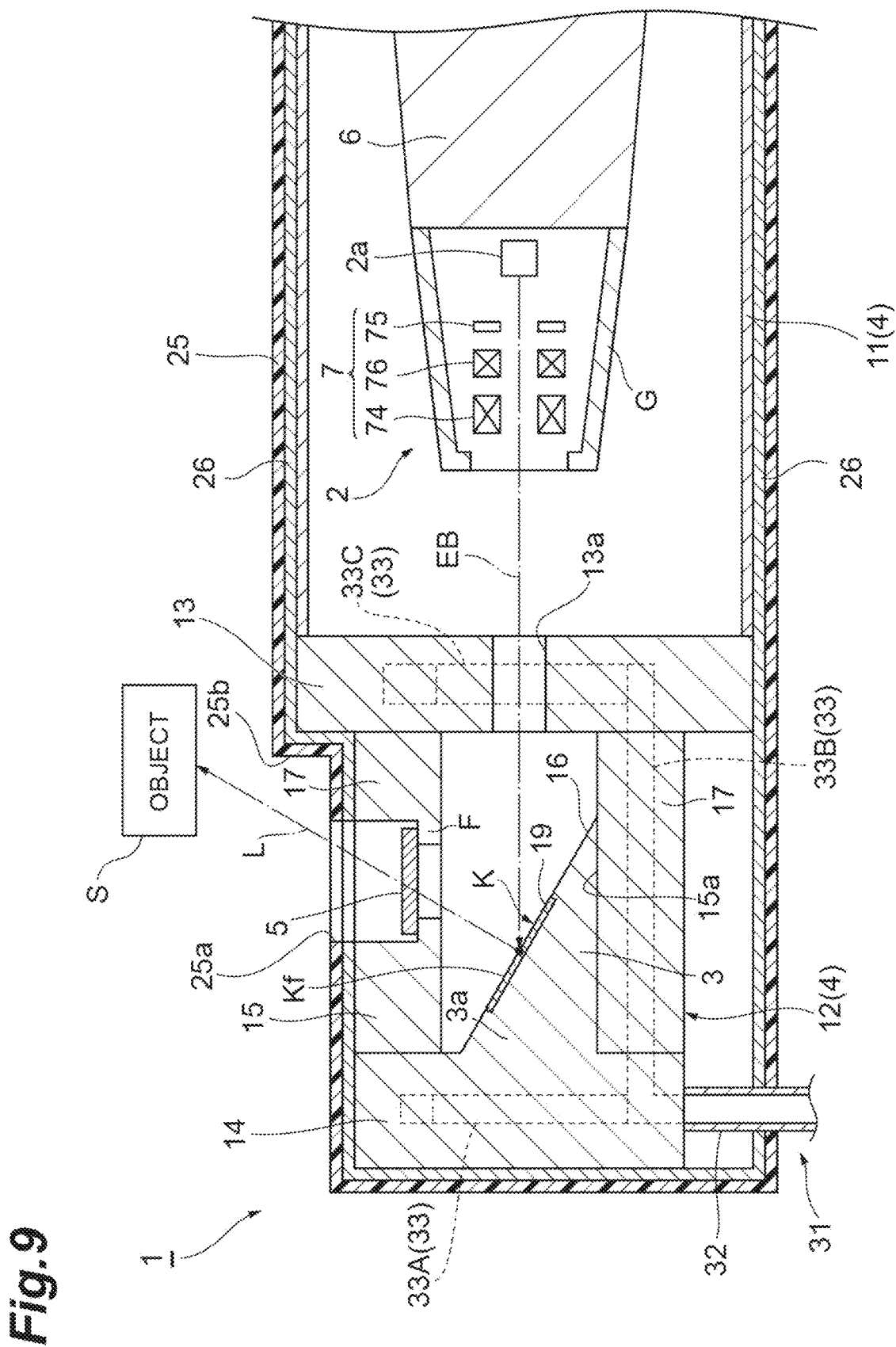
FIG. 9 is a sectional view schematically illustrating an X-ray generation device according to a modified example.

In the embodiment, the irradiation area switching unit 7 includes the deflecting coil 71, the first electrode 72, and the second electrode 73, but the configuration of the irradiation area switching unit 7 is not particularly limited. As illustrated in FIG. 9, the irradiation area switching unit 7 may include a focusing coil 74, a first electrode 75, and a deflecting coil 76. The focusing coil 74 adjusts the beam size of an electron beam EB by adjusting an amount of current flowing in the coil. The first electrode 75 adjusts an amount of electrons of the electron beam EB emitted from the filament 2*a*. The first electrode 75 is disposed between the filament 2*a* and the focusing coil 74. The deflecting coil 76 adjusts the position of the electron beam EB in a direction perpendicular to the emission axis of the electron beam EB. The deflecting coil 76 is disposed between the first electrode 75 and the focusing coil 74. The irradiation area switching unit 7 may not include, for example, at least one of the first electrodes 72 and 75, the second electrode 73, and the focusing coil 74 as long as it can switch the irradiation area ER.

Figure 10:
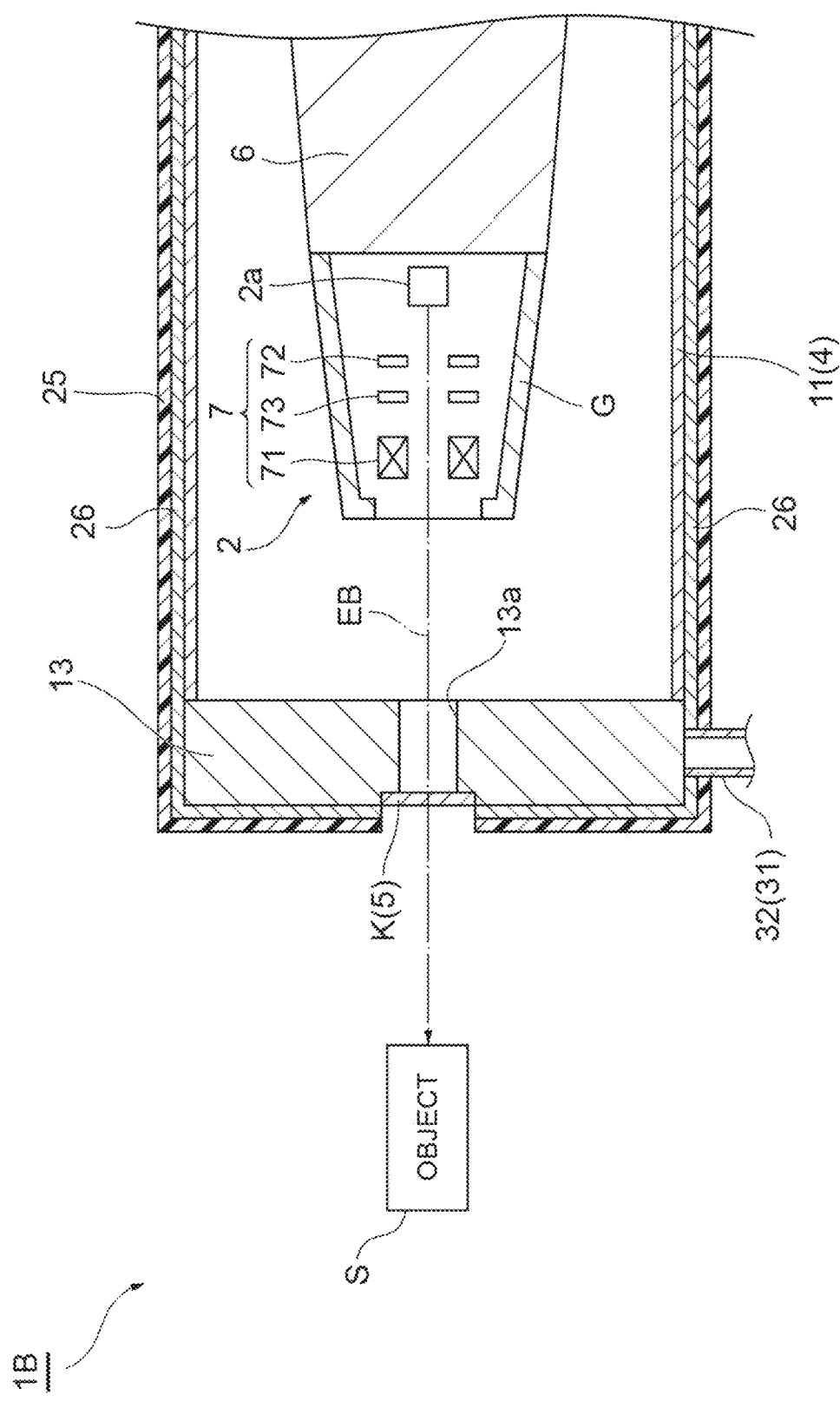
FIG. 10 is a sectional view schematically illustrating an X-ray generation device according to a modified example.

The embodiment includes the reflection type X-ray generation device 1, but the present disclosure is not limited thereto. For example, as illustrated in FIG. 10, a transmission type X-ray generation device 1B taking out X-rays L emitted in a direction based on the incidence direction of an electron beam EB on the X-ray generation target K such that the electron beam passes through the X-ray generation target K may be provided. In the X-ray generation device 1B according to the illustrated example, the X-ray generation target K also serving as the X-ray exit window 5 is disposed in the aperture part 13 such that the X-ray generation target K is perpendicular to the emission axis of the electron beam EB.

In the embodiment, the support member accommodation section 12 has a configuration in which the aperture part 13, the heat dissipation part 14, and the window holding part 15 are combined, but the configuration of the support member accommodation section 12 is not limited thereto. For example, the window holding part 15 incorporated into the aperture part 13 may be coupled to the heat dissipation part 14 to form the support member accommodation section 12, or the window holding part 15 incorporated into the heat dissipation part 14 may be coupled to the aperture part 13 to form the support member accommodation section 12. In the embodiment, the housing 4 can accommodate at least a part of the support member 3.

In the embodiment, the number of target parts included in the second irradiation area is not limited to one as long as the number of target parts included in the first irradiation area is larger than the number of target parts included in the second irradiation area and the area of the target parts included in the first irradiation area is larger than the area of the target parts included in the second irradiation area. For example, in the X-ray generation target K illustrated in FIG. 3, the number of linear target parts 22 included in the second irradiation areas ER2 may be two or more.

In the embodiment, the irradiation area is not limited to the first irradiation area and the second irradiation area, and more irradiation areas may be set such as a third irradiation area in which the number of target parts is smaller than the number of targets included in the first irradiation area and larger than the number of target parts included in the second irradiation area. The present disclosure is not limited to the linear target parts 22, 221, 321, and 421 which are formed continuously as a unified body in the longitudinal direction, but the linear target parts may be formed discretely in the longitudinal direction. In this case, it is possible to obtain X-rays under different irradiation conditions by constructing the long linear target parts 22, 221, 321, and 421 in different forms.

The configurations according to the embodiment and the modified examples are not limited to the aforementioned materials and shapes, and can employ various materials and shapes. The configurations according to the embodiment or the modified examples can be arbitrarily applied to the configurations of another embodiment or modified example. Some of the configurations in the embodiment or modified examples can be appropriately omitted without departing from the gist of an aspect of the present disclosure.

REFERENCE SIGNS LIST 1, 1B . . . X-ray generation device, 2 . . . Electron gun, 3 . . . Support member, 4 . . . Housing, 5 . . . X-ray exit window, 7 . . . Irradiation area switching unit, 21, 201, 301, 401 . . . Target part holding plate, 22, 221, 321, 421 . . . Linear target part (target part), 100 . . . X-ray imaging system, 112 . . . X-ray detector, 113 . . . Phase grating, 114 . . . Absorption grating, 222, 322, 422 . . . Dot target part (target part), EB . . . Electron beam, L . . . X-ray, ER . . . Irradiation area, ER1, ER21, ER31, ER41, ER51 . . . First irradiation area, ER2, ER22, ER32, ER42, ER52 . . . Second irradiation area, K, K2, K3, K4 . . . X-ray generation target, S . . . Object

The invention claimed is:

1. An X-ray generation device comprising:
an electron gun emitting an electron beam;
an X-ray generation target including a plurality of target parts generating X-rays in response to incidence of the electron beam from the electron gun; and
an irradiation area switching unit switching an area of the X-ray generation target irradiated with the electron beam between a first irradiation area and a second irradiation area,
wherein the number of target parts included in the first irradiation area is larger than the number of target parts included in the second irradiation area, and
wherein an area of the target parts included in the first irradiation area is larger than an area of the target parts included in the second irradiation area when seen in an incidence direction of the electron beam.

2. The X-ray generation device according to claim 1, wherein the irradiation area switching unit switches the area of the X-ray generation target irradiated with the electron beam between the first irradiation area and the second irradiation area by switching a beam size of the electron beam with which the X-ray generation target is irradiated between a first size and a second size smaller than the first size.

3. The X-ray generation device according to claim 1, wherein the irradiation area switching unit switches the area of the X-ray generation target irradiated with the electron beam between the first irradiation area and the second irradiation area by deflecting the electron beam emitted from the electron gun.

4. The X-ray generation device according to claim 1, wherein the electron gun is able to selectively emit one of a first electron beam and a second electron beam with a beam size larger than the first electron beam, and
wherein the irradiation area switching unit switches the area of the X-ray generation target irradiated with the electron beam between the first irradiation area and the second irradiation area by switching the electron beam emitted from the electron gun between the first electron beam and the second electron beam.

5. The X-ray generation device according to claim 1, wherein the X-ray generation target includes a plurality of linear target parts arranged in parallel to each other as the plurality of target parts,
wherein the first irradiation area spans to include at least two linear target parts, and
wherein the second irradiation area spans to include only one linear target part.

6. The X-ray generation device according to claim 1, wherein the X-ray generation target includes a plurality of linear target parts arranged in parallel to each other and a dot target part as the plurality of target parts,
wherein the first irradiation area spans to include at least two linear target parts, and
wherein the second irradiation area spans to include only one dot target part.

7. The X-ray generation device according to claim 5, wherein each of the linear target parts is formed continuously as a unified body in a longitudinal direction of the linear target parts.

8. The X-ray generation device according to claim 5, wherein each of the linear target parts is formed discretely in a longitudinal direction of the linear target parts.

9. The X-ray generation device according to claim 1, further comprising:
a support member supporting the X-ray generation target;
a housing accommodating at least a part of the electron gun, the X-ray generation target, and the support member; and
an X-ray exit window which is provided in the housing and through which X-rays generated from the target parts exit to the outside of the housing.

10. An X-ray imaging system comprising:
the X-ray generation device according to claim 1;
an X-ray detector detecting X-rays emitted from the X-ray generation device and passing through an object which is an imaging subject;
a phase grating provided between the X-ray generation device and the X-ray detector; and
an absorption grating provided between the phase grating and the X-ray detector.

* * * * *